United States Patent [19]
Diebold

[11] Patent Number: 5,933,565
[45] Date of Patent: Aug. 3, 1999

[54] OPTICALLY BASED METHOD AND APPARATUS FOR DETECTING A PHASE TRANSITION TEMPERATURE OF A MATERIAL OF INTEREST

[75] Inventor: Gerald J. Diebold, Barrington, R.I.

[73] Assignee: Digimelt Inc., Barrington, R.I.

[21] Appl. No.: 09/008,896

[22] Filed: Jan. 20, 1998

Related U.S. Application Data

[62] Division of application No. 08/679,571, Jul. 15, 1996, Pat. No. 5,758,968.

[51] Int. Cl.$^6$ ........................................................ G02B 6/26
[52] U.S. Cl. .......................... 385/147; 374/17; 374/208; 385/12; 385/73
[58] Field of Search .......................... 250/227.11, 227.28, 250/227.29, 573, 576; 356/43, 244, 246, 440; 374/17, 19, 20, 161, 208; 385/12, 147, 46, 47, 73, 138

[56] References Cited

U.S. PATENT DOCUMENTS

| | | |
|---|---|---|
| 2,669,863 | 2/1954 | Shapiro ........................................ 73/17 |
| 2,792,484 | 5/1957 | Gurewitsch et al. ...................... 219/20 |
| 3,161,039 | 12/1964 | Kapff .......................................... 73/17 |
| 3,187,557 | 6/1965 | Holbourne .................................. 73/17 |
| 3,289,460 | 12/1966 | Anderson .................................... 73/17 |
| 4,459,472 | 7/1984 | Morris et al. ............................ 219/535 |
| 4,572,676 | 2/1986 | Biermans et al. ........................ 374/17 |
| 4,804,274 | 2/1989 | Green ........................................ 374/17 |
| 4,808,796 | 2/1989 | Brooks et al. ........................... 219/385 |
| 4,925,314 | 5/1990 | Claudy et al. ............................. 374/16 |
| 4,927,270 | 5/1990 | Bonnard ..................................... 374/16 |
| 4,945,211 | 7/1990 | Brooks et al. ........................... 219/385 |
| 4,988,155 | 1/1991 | Harner et al. ............................. 385/12 |
| 5,022,045 | 6/1991 | Elliott ....................................... 374/20 |
| 5,092,679 | 3/1992 | Brotz ........................................ 374/19 |
| 5,288,148 | 2/1994 | Rahimzadeh ............................. 374/19 |
| 5,750,998 | 5/1998 | Goldman .................................. 250/343 |

FOREIGN PATENT DOCUMENTS 58-162824  9/1983  Japan .

*Primary Examiner*—Hung N. Ngo

[57] ABSTRACT

The melting point of a test substance is determined by placing it in a capillary tube within a heated block. The temperature of the block and sample are gradually increased using an electrical heater. The output of a light emitting diode or solid state laser is coupled into an optical fiber that carries the radiation to the capillary tube containing the test substance. A second fiber that is connected to a detector collects radiation from the capillary tube. At the melting point of a solid, or possibly at the boiling point of a liquid, the light scattering and transmissive properties of the test substance change causing the light signal collected by the second fiber to change. The phase transition point is recorded as a change in the output voltage from the detector. The melting point detector is equipped with a number of ports for capillary tubes, fibers, light emitters and detectors so that many phase transition points of different samples can be determined in one heating cycle. The outputs from the detectors are input to a computer and the detector signals are correlated with the temperature of the block.

19 Claims, 7 Drawing Sheets

OPTICALLY BASED METHOD AND APPARATUS FOR DETECTING A PHASE TRANSITION TEMPERATURE OF A MATERIAL OF INTEREST

CROSS-REFERENCE TO A RELATED PATENT APPLICATION

This patent application is a divisional of copending and allowed U.S. patent application Ser. No. 08/679,571, filed Jul. 15, 1996, now U.S. Pat. No. 5,758,968.

FIELD OF THE INVENTION

This invention relates generally to apparatus and methods for detecting thermal properties of materials and, in particular to the determination of the melting point of a solid or the boiling point of a liquid by means of changes in the transmissive and/or reflective properties of the solid or liquid.

BACKGROUND OF THE INVENTION

Many methods have been employed to determine the phase transition temperatures of solids and liquids. One well known approach employs a heated block or liquid to increase the temperature of a test substance. As the temperature of the substance is increased, at some point, the phase transition temperature is reached and the transmissive and reflective optical properties of the substance change. During this process the volume of the sample may change somewhat, as can occur in the case of a powdered solid as the interstitial spaces between the particles fill with liquid. The phase transition point can be recorded by an operator who observes the substance and notes the temperature at which a visual change in the sample takes place. This method is reliable, but lacks accuracy, is somewhat subjective, and requires the constant attention of the operator. The process is also inherently limited in the number of samples that can be tested, since each sample must be constantly observed.

U.S. Pat. No. 2,669,863 to Shapiro teaches that a beam of light can be used with a photocell to monitor the change in light transmission when a phase transition takes place. This instrument used a direct beam of light from a lamp to illuminate the test substance. A photocell, suitably amplified, records the change in transmission of the sample when the phase transition point is reached.

Similarly, the use of the change in reflective properties of a liquid for determination of a "pour point" of the liquid was described in U.S. Pat. No. 3,161,939 to Kapff. The apparatus employs a light source and a condensing lens to direct the light onto the sample. A change in the light intensity reflected by the surface of the liquid, when the pour point of the liquid is reached, was then recorded.

Both of these instruments eliminated the necessity for constant attention by an operator and thus made accurate, automated measurements possible. However, the possibility of simultaneously testing a number of samples in a single heated block at the same time was at best problematic, owing at least to the large size of conventional optics which do not admit themselves to miniaturization when used in conjunction with small samples in a heated block.

A method of measuring the melting point of a chemical taking advantage of the volume change in a solid sample was described by Anderson U.S. Pat. No. 3,289,460. In this method, a solid bar is in contact with the solid. The change in properties of the solid on changing state causes a motion of the bar. At the end of the bar away from the sample an electrical switch changes state in response to the motion of the bar, thus indicating the point of the phase transition.

Measurement of phase transition points of hydrocarbons and fuel mixtures is the object of U.S. Pat. No. 4,804,274 to Green. This patent describes a phase transition point detector where a laser beam directly illuminates the sample in a straight optical path, and where a photodetector is also placed in the direct path of the laser beam. In an earlier patent, U.S. Pat. No. 3,807,865, Gordon also employed a laser as the source of radiation. In both cases, the laser requires a direct, unobstructed path to the sample, which makes the miniaturization of the light source and detector difficult, with the consequence that a limited number of ports can be built into the detector.

It has been noted in the prior art that the temperature of the phase transition point depends on the pressure. For example, U.S. Pat. No. 5,092,679 to Brotz teaches a melting point detection device where pressure can be applied to the sample as it is being heated. The sample is placed on a plate with a reflectance that is lower than that of the powdered sample. The change in reflectance of the plate-sample combination on melting permits light to reach a lower chamber, thereby lowering the intensity of light in an upper chamber which contains a light source and a detector. The use of pressure information in the recording of melting points has also been the object of an earlier patent by Hancock, in U.S. Pat. No. 4,484,822.

Rahlmsadsh, in U.S. Pat. No. 5,288,148, describes a melting point detector where the sample is placed on a glass slide, which is mounted horizontally. A light beam directed from the underside of the slide illuminates the slide and sample at an angle to the normal. The reflected light is detected at the reflection angle by a photodetector whose intensity is recorded in time. When the melting point is reached, the change in reflective properties of the test substance changes, and a change is recorded in the output voltage of the light detector.

OBJECTS OF THE INVENTION

It is a first object of this invention to provide improved methods and apparatus for detecting a phase transition in a substance or material of interest.

It is a further object of this invention to provide optically-based methods and apparatus for simultaneously determining a phase transition temperature of a plurality of samples.

SUMMARY OF THE INVENTION

The foregoing and other problems are overcome and the objects of the invention are realized by methods and apparatus in accordance with embodiments of this invention. In one aspect this invention teaches a method for automatically determining and recording one or more phase transition points, that is, the temperature at which phase transitions take place in solids and liquids. Such phase transition points are commonly referred to as melting and boiling points, respectively.

In accordance with a further aspect of this invention a high thermal conductivity block is provided with a heating element and a plurality of sample ports for holding a plurality of samples; a source of optical radiation; bidirectional optical paths for transferring the optical radiation to the sample ports and for gathering scattered and/or transmitted radiation from the samples; a detector of the radiation received back from the samples; and a device for recording the temperature and the radiation from the sample.

In accordance with a further aspect of this invention there is provided a method for determining the temperature at which a substance within a heated block changes state. The method includes the steps of monitoring the change in optical properties of the substance through optical fibers, one of which carries radiation to the sample and a second one of which carries light from the sample. The intensity of the light received from the sample is monitored by a photodetector whose output is recorded by a computer equipped with a suitable analog-to-digital converter for data acquisition. Because the optical fibers permit the light source (or sources) and detectors to be located remotely from the heated block, the heated block can be equipped with many ports, pairs of optical fibers, light sources and detectors. This advantage is further facilitated by use of small light sources and detectors that are compatible with optical fibers. An important advantage of the use of optical fibers in the construction of a melting point apparatus is that a large number of samples can be tested simultaneously, thereby significantly reducing the total time for testing of a number of samples.

Although the apparatus can be constructed so as to provide a large number of ports, samples, fibers and detectors, the relative slowness of the change in optical properties of the samples during a phase change permits the outputs of many detectors to be fed to a computer-based analog-to-digital converter with multiple inputs for acquiring and storing the data for each detector.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The ensuing description of this invention will describe several embodiments, including a reflective/transmissive (RT) mode embodiment, a transmissive (T) mode embodiment, and a polarization (P) mode embodiment. The operation of the invention in the RT mode is as follows.

Figure 1:
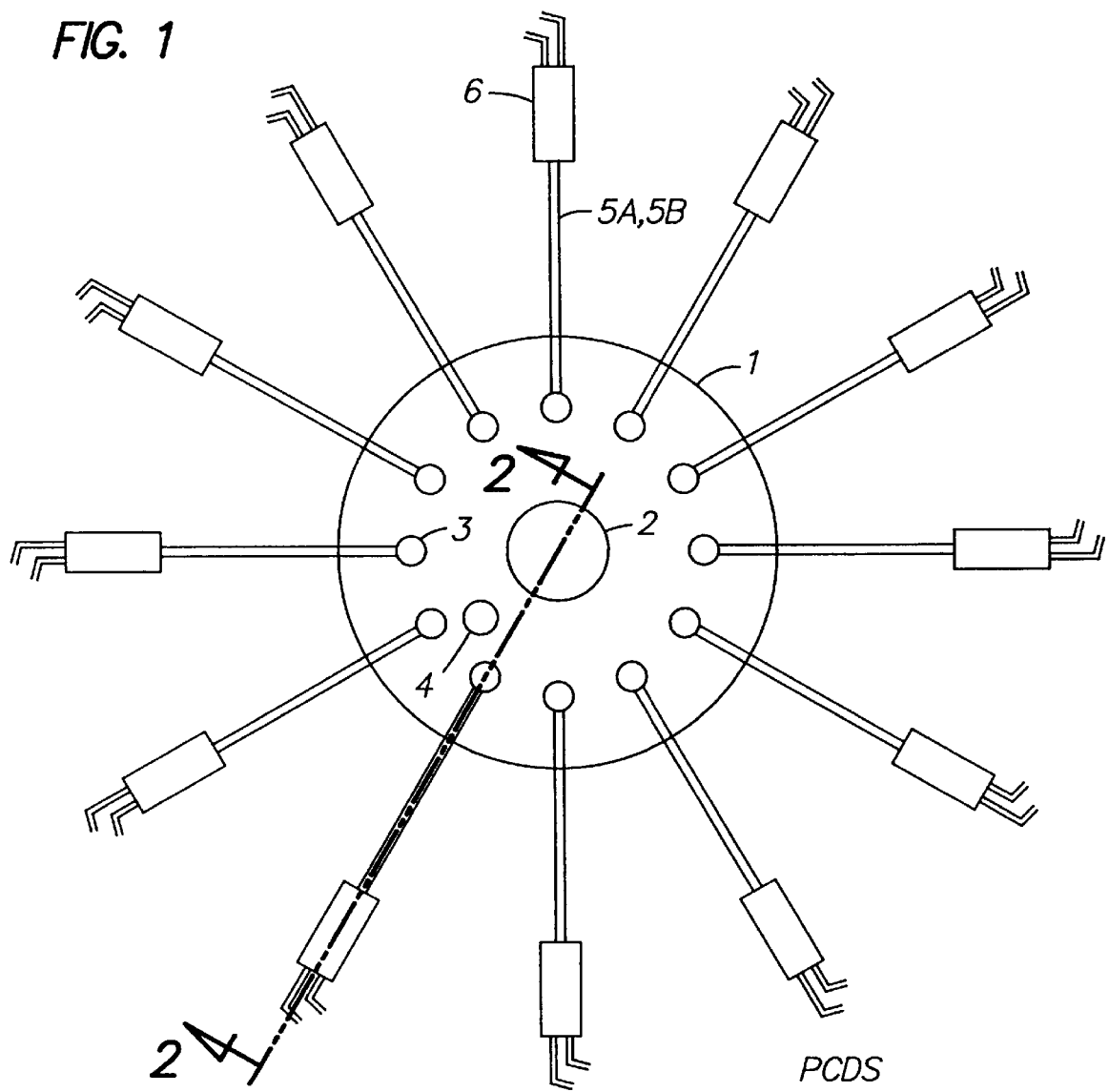
FIG. 1 is a top view of an apparatus according to one embodiment of this invention, wherein a circular heating block has a plurality of sample chambers and a plurality of optical fibers are positioned so as to monitor the phase transition of samples in a reflective/transmissive mode.

Referring to FIG. 1, a phase change detection system (PCDS) includes a circular cylindrical heater block 1 comprised of metal or some other heat conducting material that exhibits a high thermal conductivity. The block 1 is thus uniformly heated by at least one electrical heating element 2. An exemplary, but not limiting, size of the block 1 is approximately 1.5" (diameter) by 3" (length). The block 1 has holes arranged generally in an axisymmetric or circular pattern for supporting capillary tubes 3 that contain the substance or substances to be tested. Such capillary tubes are conventionally 1.5–3 mm in diameter and have a length of about three inches. The hole s that contain the capillary tubes 3 are preferably only slightly larger in diameter than the capillary tubes. Due to the close proximity of the sample substances to the heated block 1, the samples are thermally coupled to the block 1 and are also heated therewith. At least one temperature sensor 4, such as a well-known thermocouple or a resistance thermometer, is provided for measuring the temperature of the block 1. Power to the heating element 2 is controlled in a conventional manner by an external electrical circuit (see FIG. 8) that senses the temperature via the temperature sensor 4, compares the temperature of the heater block 1 to a desired, externally programmed temperature, and then adjusts the input power to the heater 2 appropriately so as to ramp the temperature upwardly at a controlled, predetermined rate.

Although described primarily in the context of a heating element for elevating the temperature of the block 1, it should also be noted that the element 2 could as well be a cooling element for reducing the temperature of the block 1, thereby enabling a measurement of the freezing temperature of a substance or substances of interest.

As the temperature of the heater block 1 is increased, the temperature of the test substances in the capillary tubes 3 also increases accordingly and at some temperature, characteristic of the substance, a phase change takes place. The occurrence of the phase change of the substance in the capillary tube 3 is determined by a change in its optical properties. The optical properties of the substance are monitored by a light emitter and a light detector located in a mounting block 6. As can be better seen in FIG. 2, the light emitting device 9 transmits optical radiation (visible, ultraviolet, or infrared radiation) to the capillary tube 3 through a "transmitter" optical fiber 5A or bundle of fibers which use the property of total internal reflection of electromagnetic radiation to convey radiation to the terminal end of the fiber where the capillary tube 3 and test substance 8 are located. Light is thus brought by the optical fiber 5A from the light emitting device 9 directly to the capillary tube 3.

The PCDS also includes a second, "detector" optical fiber 5B or bundle of fibers that receives light that is scattered or reflected from the test substance 8, and/or from the inside surface of the capillary tube hole 3A, and conveys this light back to an optical detector (photodetector) 11 located in the mounting block 6.

At temperatures not at the phase transition temperature, the light signal reaching the photodetector 11 is, on average, constant over time. This is true even if the light emitting device 9 is operated intermittently in a pulsed-mode of operation. The voltage output from the photodetector 11 is thus approximately constant over time.

However, at the phase transition temperature a change in the transmissive and or reflective optical properties of the test substance 8 takes place. This change in the test substance alters the amount of light collected by the detector fiber 5B, thus altering the light signal received by the photodetector 11 and hence changing its output voltage.

In this regard it can be noted that many compounds are solids that scatter radiation when they are in the form of powered solids, but after melting appear as a clear liquid. Large changes in the detected radiation can thus be recorded since there can be a great difference in the amount of light collected by the detector fiber 5B when light is reflected from the surface of the solid, as compared to when the light penetrates the capillary tube 3 through the now-liquid substance, impinges the inner wall of the hole 3A, where it is partially absorbed, and is then scattered and or reflected back into the detector fiber 5B.

Figure 5:
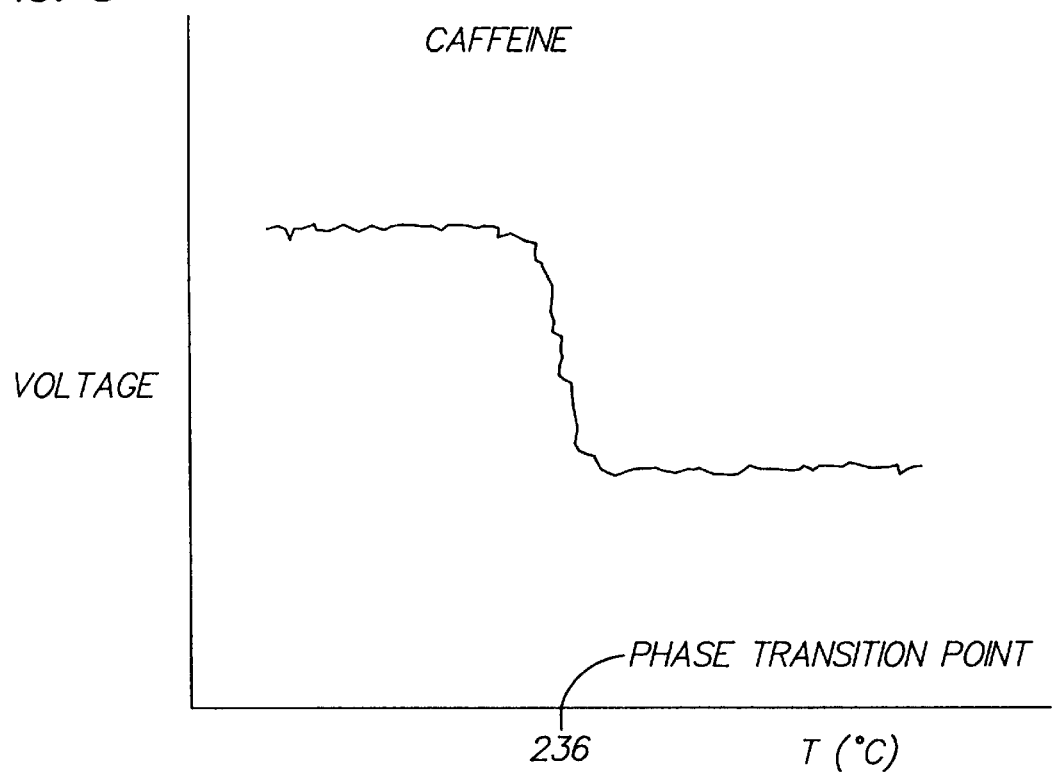
FIG. 5. is representative graph showing a change in photodetector output voltage versus temperature for a sample within one of the sample chambers of the embodiment of FIG. 1.

As can be seen in the caffeine example of FIG. 5, a record of the temperature of the detector block 1 versus photodetector voltage clearly indicates the temperature where the phase transition takes place. This is made manifest by a significant change in the detector voltage. The precise melting, boiling, or freezing point of the substance of interest can thus be determined and recorded.

With regard to the boiling point, and by example, the presence of bubbles within a liquid sample can cause a change in the amount of light that is transmitted through the sample (assuming that the sample is not opaque). As such, this change in the amount of transmitted light can be indicative of the liquid sample being elevated to a phase transition temperature.

Well known computer-implemented techniques permit the use of feedback and preprogrammed temperature ramps to control the temperature of the block 1. The recording of the output of the photodetector 11 can be carried out by using an analog-to-digital converter, thus permitting the photodetector signal, as well as the temperature as measured by the sensor 4, to be recorded, stored and analyzed. In other embodiments a conventional analog recording (e.g., as by a strip chart recorder) of the photodetector output can be used as well to determine the phase transition point.

An expressed object of this invention is to provide a system where a number of samples can be large. This is accomplished by providing a desired number of capillary sample ports and the associated photoemitters, photodetectors, and fiber optics. The 12 twelve capillary ports in a cylindrical geometry shown in FIG. 1 should thus be viewed as being exemplary; and more or fewer ports can be provided, as desired.

Figure 2:
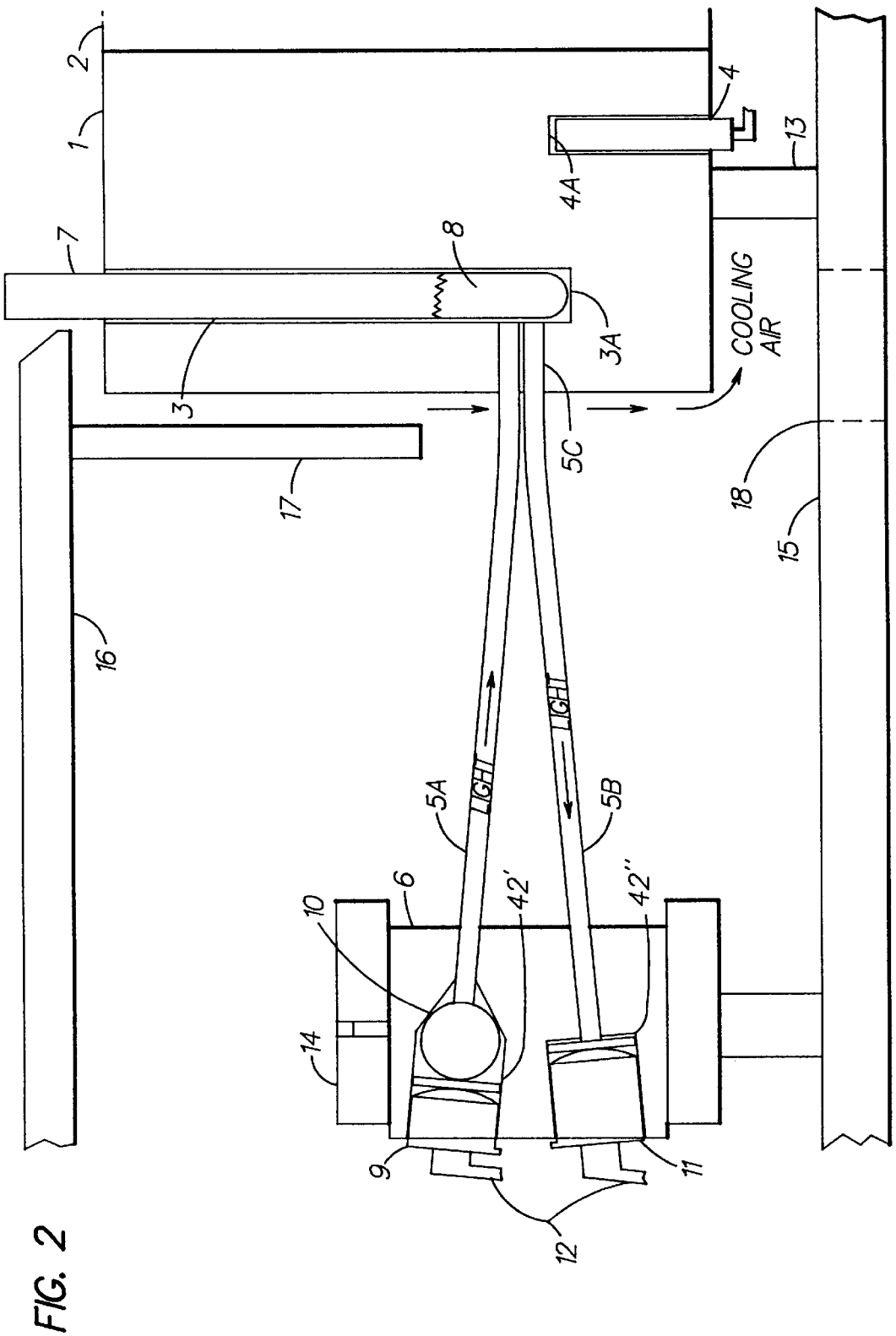
FIG. 2 is a partial cross-sectional view of the apparatus of FIG. 1, taken along the section line 2—2, for illustrating one sample chamber element.

Still referring to FIG. 2, the heater block 1 has the hole 3A for the capillary port 3 drilled into it, as well as a hole 4A into which is placed the sensor 4 for measurement and control of the heater block temperature. The transmitter optical fiber 5A and the detector fiber 5B are fitted into an aperture 5C made into the side of the heater block 1 so as to view the test substance 8 through the capillary port 3. The other ends of the fibers 5A, 5B are fixed into the mounting block 6.

For operation of the PCDS a transparent capillary tube 7 is filled partly with the test substance 8 and is placed into the capillary port hole 3A. The light emitting device 9, which may be an incandescent lamp, a light emitting solid state diode, or a solid state laser, generates optical radiation that may be directly coupled into the fiber 5A, or that may coupled by means of a focusing element such as a lens 10.

The radiation traverses fiber 5A to the test substance 8, and the reflected/transmitted radiation is collected by the end of the fiber 5B and transmitted to the photodetector 11. A focusing element (not shown) may be used as in the case of the emitter 9 to improve coupling of radiation from the fiber 5B to the radiation-responsive surface of the photodetector 11. Wiring 12 to the light emitter 9 and from the photodetector 11 are connected to a power supply (not shown) and a recording device (e.g., a computer-controlled data acquisition system (FIG. 8)), respectively.

The heater block 1 is normally supported by an insulating post 13. The mounting block 6 is held in place as well by a support 14. These components are mounted on a plate 15. A cover 16 is preferably provided to prevent the operator from coming into contact with the hot surface of the heater block 1. After the phase transition point of the test substance 8 has been reached, the heater block 1 is cooled down, for example with a fan, so that new samples can be tested. Thus, the PCDS can be equipped with an air flow baffle 17 to direct cooling air along the surface of the heater block 1 and down through a cut-out 18 within the bottom plate 15 during the cooling cycle.

Figure 3:
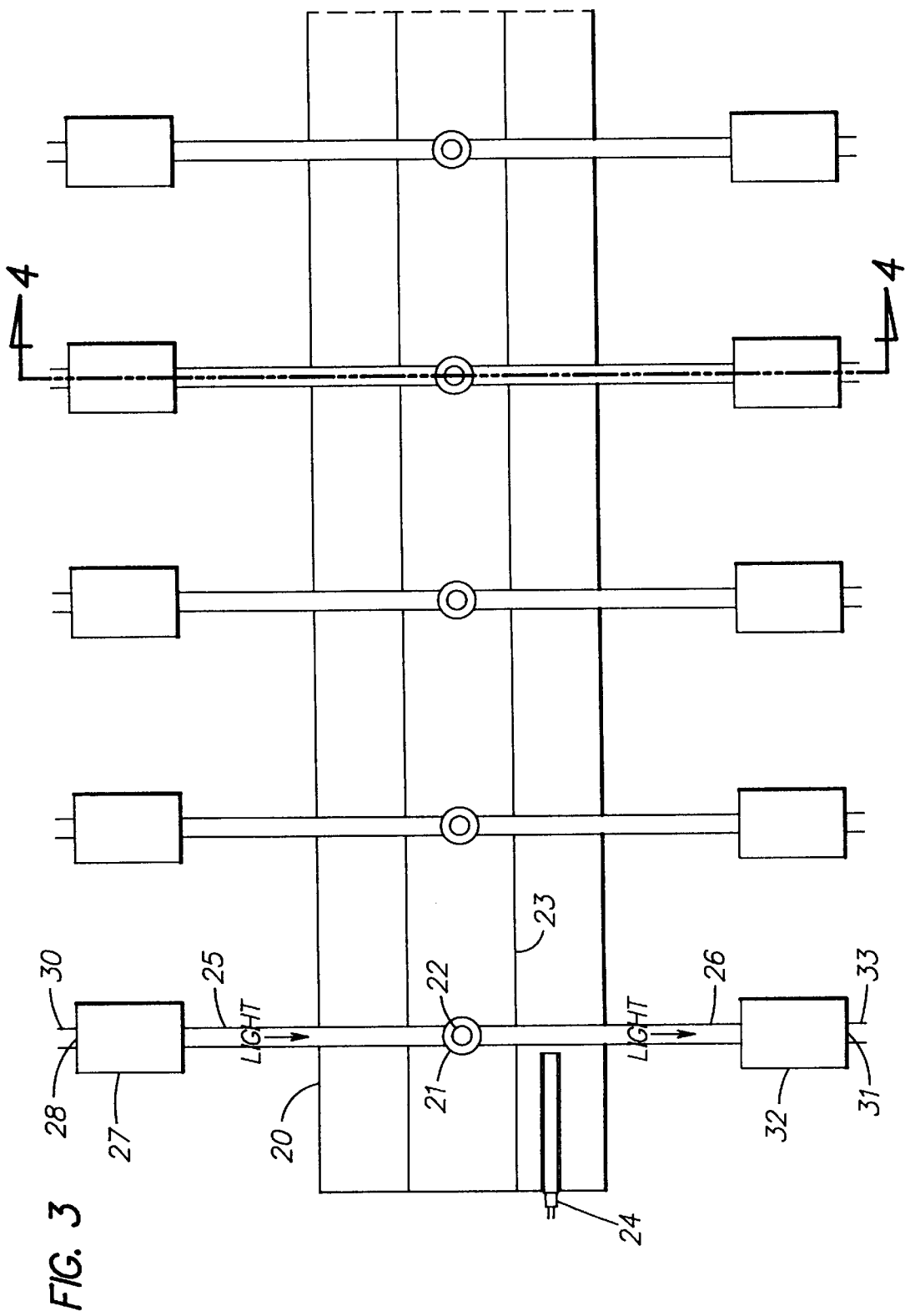
FIG. 3 is a top view of an apparatus according to a second embodiment of this invention wherein a linear heating block has a plurality of sample chambers and a plurality of optical fibers are positioned so as to monitor the phase transition of samples in a transmissive mode.
Figure 4:
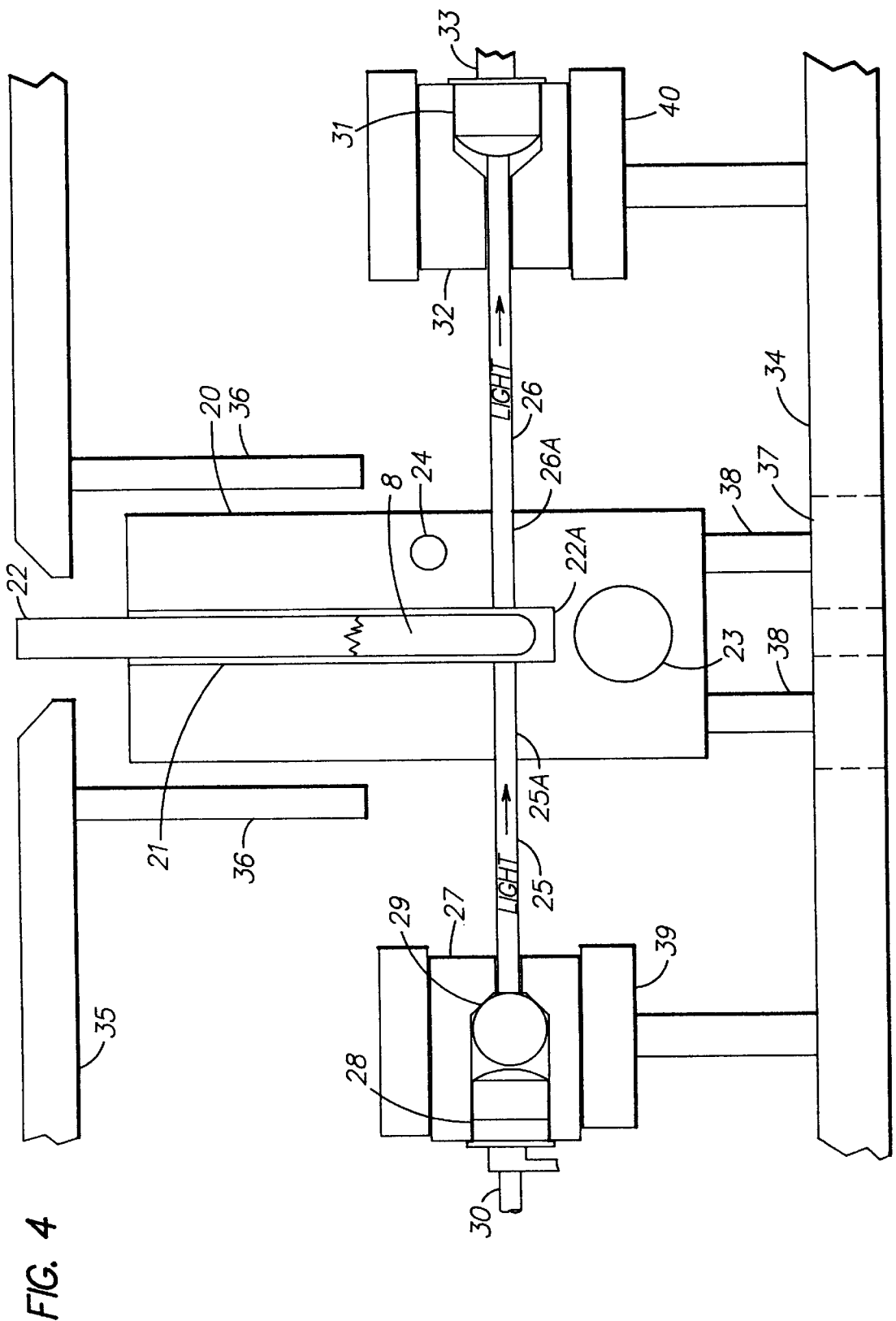
FIG. 4 is a partial cross-sectional view of the apparatus of FIG. 3, taken along the section line 4—4, for illustrating one sample chamber element.

In a second embodiment of the invention a linear geometry is employed for placement of the capillary ports 3 and mounting blocks 6, as is shown in the top view of FIG. 3 and the cross-sectional view of FIG. 4. In this embodiment the heater block 20 is in the shape of a bar, with the capillary ports 21 placed linearly along its length, each containing a capillary tube 22, and a heating element (or elements) 23 that extends along the length of the bar so as to heat it uniformly. A temperature sensor 24 is mounted in the heater block 20 to provide a temperature measurement and to provide a signal to a feedback device that controls the block temperature. An optical transmitter fiber 25 and an optical detector fiber 26 are positioned in the heater block 20 so as to view the test substance 8 in the capillary tube 22. The optical transmitter fiber 25 conveys optical radiation from the optical emitter 28 in a first mounting block 27. Power is fed to the emitter through wiring 30. Radiation is directed onto the test substance 8 from the transmitter fiber 25.

Figure 6:
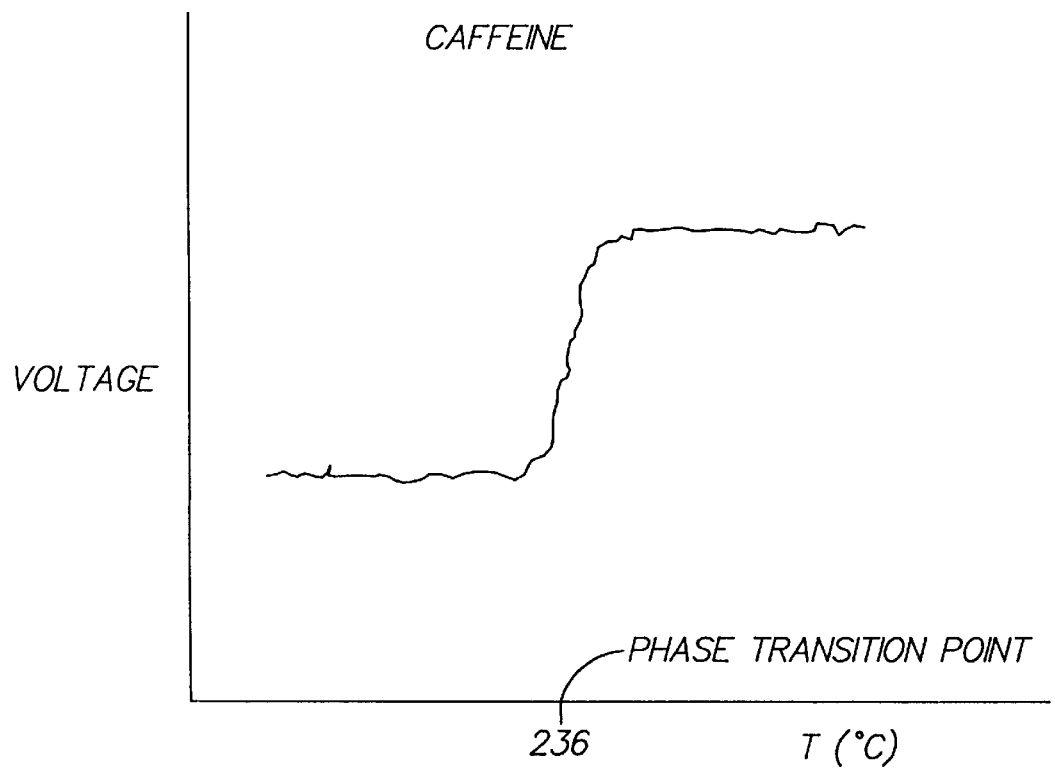
FIG. 6. is representative graph showing a change in photodetector output voltage versus temperature for a sample within one of the sample chambers of the embodiment of FIG. 3.

When the test substance 8 is first placed in the heater block 20 it may be an opaque powered solid. In this case the optical radiation is not transmitted through the sample to the detector fiber 26, and a negligible electrical signal is produced by the photodetector 30 mounted in block 31. At some point as the temperature of the heater block 20 is increased, the phase transition temperature of the test substance 8 is reached and the optical transmissive properties of the test substance 8 are altered. Typically, the substance 8 becomes a clear liquid upon melting. At this time a greater amount of light is received by the photodetector 31 and its output voltage at wiring 33 increases. In this embodiment of the PCDS the phase transition point is determined by the transmissive properties of the test sample 8, as opposed to its transmissive and reflective properties in the first embodiment described above. A representative output signal is shown in FIG. 6.

As is depicted in FIG. 3, the heater block 20 can be provided with a plurality (e.g., five) of transmitter and detector units that are disposed along the length of the heater block 20 in order to test a number of samples at one time. The cross-sectional view of FIG. 4 details one of the transmitter receiver units. The heater block 20 has a capillary port 21 defined by a hole 22A that encloses a portion of the length of the capillary tube 22. The heater block 20 is uniformly heated along its length by the electrical heater 23. The temperature sensor 24 is placed in the heater block 20 and is used by external electronics (FIG. 7) to sense the temperature of the block 20. The heater block 20 has holes 25A and 26A for the transmitter optical fiber 25 and the detector optical fiber 26, respectively. These holes are positioned so that the ends of the fibers 25 and 26 view the test substance 8. The opposite end of the transmitter fiber 25 is mounted in a mounting block 27 which houses the light emitting device 28 and, as an option, a lens 29. Power is fed to the light emitting device 28 through wiring 30. The photodetector 31 is held in a mounting block 32 and receives light emitted from the light emitter 28 through the sample 8, via the optical fibers 25 and 26, and produces a voltage at its output wiring 33. The voltage is proportional to the intensity of the light transmitted through the sample 8.

A suitable calibration can be made, without the sample 8, so as to determine the amount of any losses between the emitter 28 and the photodetector 31.

As in the embodiment of FIGS. 1 and 2, the embodiment of FIGS. 3 and 4 also preferably includes a bottom support plate 34 having at least one cooling air exhaust aperture 37, a top plate 35, cooling air baffles 36, thermally insulating supports 38 for the block 20, and mounting brackets 39 and 40 for the emitter and detector blocks 27 and 32, respectively.

In the third mode of operation, referred to above as the polarization mode, the temperature of a phase transition point of a sample is made using the polarization properties of the sample. In this embodiment, which may be best practiced using the embodiment of FIGS. 1 and 2, the incident radiation on the sample 8 is made to be polarized. Since a powdered sample possesses many facets that are oriented at many different angles to the polarization vector of the incident radiation, and since the reflected intensity of polarized light depends on the angle of incidence of that the radiation makes with the scatterer, the multiple facets of the powder scatter radiation into the detector fiber 5B with a characteristic intensity and polarization. The detector fiber 5B carries the scattered radiation to the detector block 6 which has a polarizing element placed in front of the photodetector 11. Thus, the intensity of radiation characteristic of the solid sample 8 is recorded while the sample is in the solid state. When a phase transition takes place, the facets of the solid sample are no longer present and the sample returns an amount of light to the detector fiber 5B that is characteristic of the liquid phase of the sample. The change in the amount of radiation received by the photodetector 11 is thus correlated with the temperature of the block 1, and can be equated with the phase transition point temperature.

An embodiment of the polarization mode PCDS is as shown in FIGS. 1 and 2, and as described above in the context of the reflection/transmission mode of operation, except that polarizing elements are placed in the path of the optical radiation in both the transmitter and detector fibers 5A and 5B. Thus FIG. 1 is modified to contain a polarizing element 42' between the light emitting device 9 and the transmission optical fiber 5A, and a second polarizing element 42" between the end of the detector optical fiber 5B and the photodetector 11. In this case the optical fibers 5A and 5B are selected to be of the type that preserve the polarization of radiation.

Figure 7:
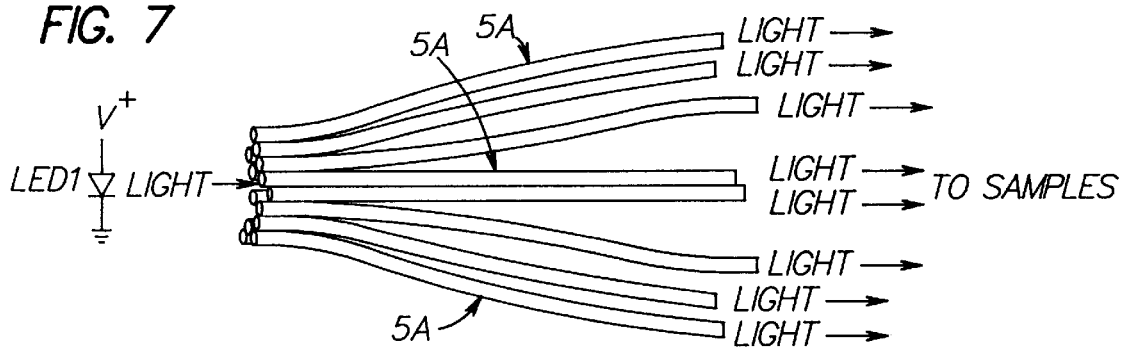
FIG. 7 illustrates a single photoemitter providing optical radiation to a plurality of optical fibers associated with a plurality of sample chambers.

FIG. 7 illustrates a single photoemitter, for example a light emitting diode (LED1), that provides optical radiation to a plurality of the optical fibers 5A (or 25) that are associated with a plurality of sample chambers. This embodiment thus eliminates a necessity to provide n photoemitters for a block having n sample chambers. The single LED1 need not supply all of the sample chambers, for example two LEDS could be provided, with one supplying half the sample chambers and the other supplying the other half.

Figure 8:
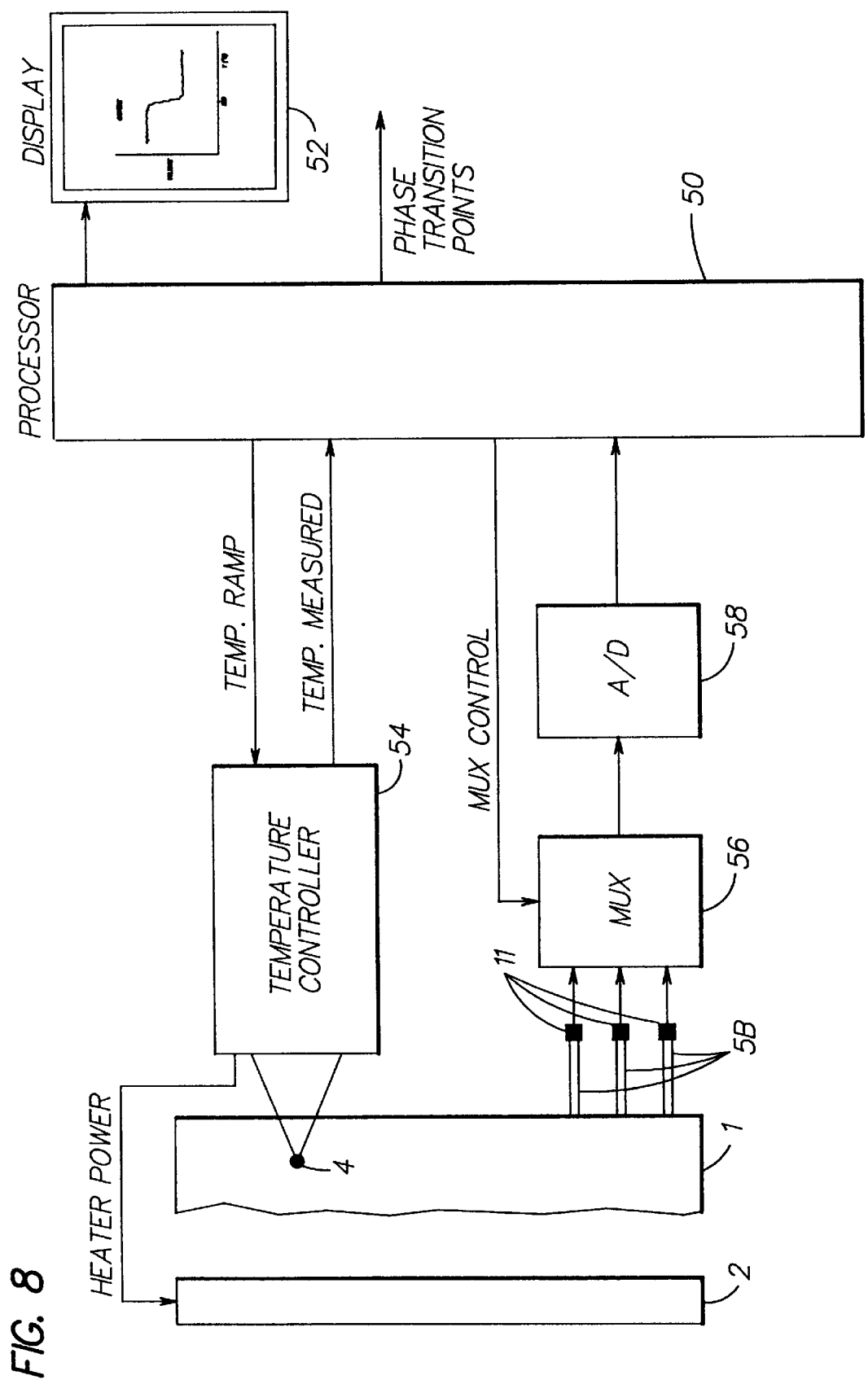
FIG. 8 is a block diagram of one suitable embodiment of a data acquisition system for use with the apparatus of FIGS. 1–4.

FIG. 8 is a block diagram of the PCDS system in accordance with an embodiment of this invention. FIG. 8 is disclosed in the context of FIGS. 1 and 2, although the system of FIGS. 3 and 4 can be used as well. A processor 50 is coupled to an optional display 52 for graphically displaying phase transition point measurement results. The processor 50 also has an output for outputting this data to, for example, a printer or any suitable data sink, such as a mass storage unit. A temperature control unit 54 is programmed by the processor 50 (signal T RAMP) and controls the heater power accordingly. The temperature controller 54 has an input coupled to the temperature sensor 4 for determining the temperature of the block 1. The measured temperature is reported back to the processor 50. The outputs of the photodetectors 11 are coupled to a suitable multiplexer (MUX) 56 that is controlled by the processor 50. The use of the multiplexer 56 is optional, as separate parallel signal channels can be provided if desired. A selected one of the photodetector output voltages is digitized by an A/D convertor 58 and is input to the processor 50. The processor 50 monitors the output of the A/D convertor 58 for individual ones of the samples being measured. When a distinctive change in the output voltage is detected, as shown in FIG. 5 for a caffeine example, the processor 50 records the measured temperature and thus determines the phase transition point for the particular sample whose output photodetector 11 is currently selected. The distinctive change is preferably a change in the photodetector voltage that varies by some threshold amount that is specified within some interval of time. The specific values can be determined empirically. In operation, the processor 50 preferably operates the MUX 56 to cycle through the photodetector outputs and to record their respective output voltage magnitudes.

A number of techniques can be employed by the processor 50 to determine the melting point of a sample. The following techniques are exemplary.

In a first technique, the processor 50 acquires the detector signal versus temperature, and calculates the first derivative of the signal with respect to temperature. The absolute value of the derivative is then taken, which will be a predominately flat curve with a peak at the melting point. The position of the maximum of the peak can be determined using a maximum value search. This point on the temperature axis is then taken as the melting point.

In a second technique, the average initial and average final signal values at the starting and ending temperatures is found, and the difference between these temperatures is taken. Some percentage (e.g., 10%) of the difference is used as a reference, and the processor 50 then determines when the signal changes from its original value by 10%. The temperature where this 10% change in the diode signal occurs is then taken as the melting point.

In a third technique the entire melting point curve is fit to a predetermined functional form, with a standard least squares method being used to determine the best fit. Once the curve has been fit to the functional form, and the numerical coefficients in the function have been determined, the melting point is calculated from the coefficients. By example, a step function can be employed, with the function starting at one positive value and decreasing in a step to a second constant value.

A more optimum curve fitting routine fits the derivative of the signal with resect to temperature with a peaked curve such as a Gaussian or a Lorentzian. The peak in the Gaussian or the Lorentzian is at the melting point, which can be determined from the coefficients after the numerical fit.

Another technique employs the computation of a tangent to the signal versus temperature curve, the determination of the maximum value of the tangent, and extrapolation of the tangent line back to the baseline to give the melting point temperature.

The above mentioned curve fitting routines have the advantage that they smooth the curve so that the effects of noise and spikes are reduced. It should be noted that two or more of the foregoing techniques could be used in combination to determine the phase transition temperature of a substance of interest.

In presently preferred embodiments of this invention the following components have been found to provide satisfactory results. with regard to an infrared light source, an Optek, Inc. OP 231, OP 231, or OP 233 infrared light emitting diodes (LED's) have been found to be satisfactory, while the OP 233 is preferred. These devices are GaAlAs LEDs that emit in the wavelength region around 890 nm with an approximately 90 nm wide bandwidth. The OP233 has an output, according to the manufacturer, of 10 mW or 6 mW/cm$^2$ in the forward direction.

One further, but not limiting, embodiment of the light emitting device 9 is a GaAlAs solid state laser, such as a Spectra Diode Labs SDL 5400-G1, with a 50 mW output power. The use of this laser diode can readily power all of the fibers simultaneously, as in the configuration of FIG. 7.

A suitable photodetector is an Optek, Inc. OP 505A NPN Si phototransistor. This device has a peak sensitivity at 850 nm and has a detection bandwidth of about 300 nm. The photodetector's optical response is thus fairly closely matched to the above LED's emission spectrum.

For operation with a visible light source it has been found that a Hewlett-Packard HLMT-CHOO LED operating at 630 nm with a 20 nm bandwidth provides adequate performance. In this case a United Detector Technology, Inc. PIN-3D is one suitable photodetector, since it has a significant response in the visible spectrum. Other photodetectors that are more closely optimized for detecting the 630 nm radiation can also be used.

Although it has been found that there is no significant difference in operating the PCDS with visible or infrared components, the use of infrared components is presently preferred in that the power of the infrared LED's is greater than that of most available visible LED's. Furthermore, infrared photodetectors are generally more sensitive than visible phototransistors. Thus, although visible emitters and detectors are suitable for use, they generally provide relatively smaller signal levels than the IR devices. The generation of a large output voltage signal is desirable in that it lowers the gain requirements of the signal processing electronics, in particular the A/D converter, thus possibly eliminating a need to provide signal amplifiers.

One suitable optical fiber is a 3M Corp. FG 400 LAT multimode fiber with the plastic cladding removed. The fiber diameter is 400 microns.

In this regard, the diameters of the holes through which the optical fibers are brought to the sample chambers are preferably only slightly larger than the fiber diameter. Thus, for the transmissive/reflective mode of operation these holes are slightly larger than two fiber diameters, while for the transmissive mode of operation the holes are slightly larger than one fiber diameter.

Figure 9:
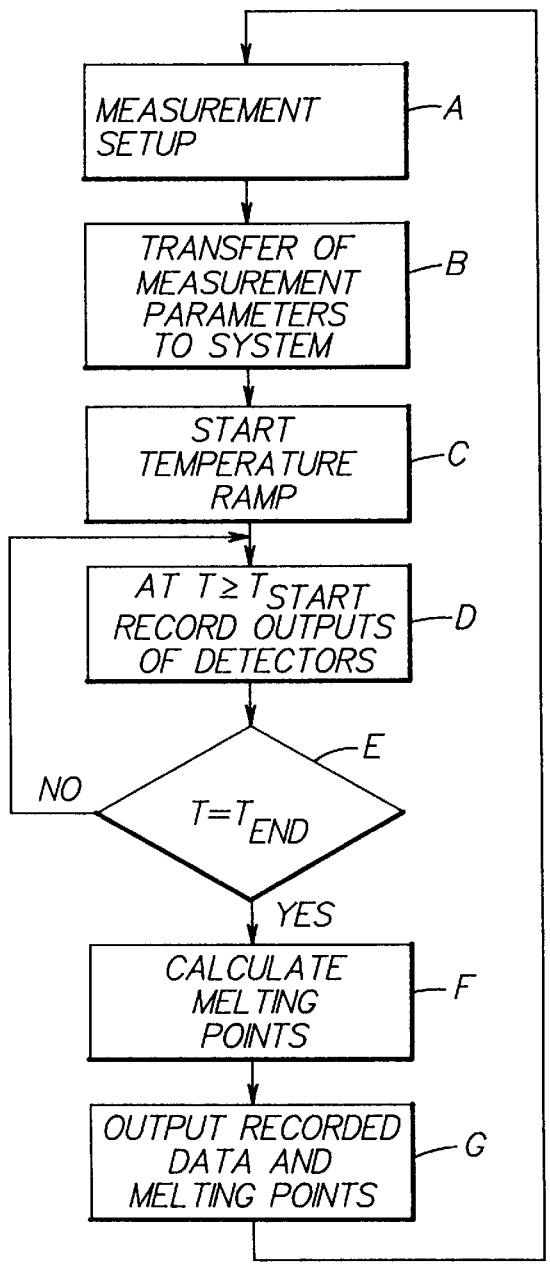
FIG. 9 is a flow chart illustrating a method in accordance with this invention.

FIG. 9 is a flow chart that illustrates a method for operating the system shown in FIG. 8.

Block A is a measurement set-up step, wherein an operator selects initial and final temperatures, the resolution of the measurement (e.g., 0.1° C., 0.5° C., etc.) and the ramp rate of the temperature controller 54. Identifications of the various samples, correlated with capillary tube hole or sample chamber positions, are also entered, as can be other information, such as the desired output data format.

At Block B the information is entered into the system, the temperature controller 54 is programmed appropriately, and at Block C the temperature controller begins to ramp up the temperature of the block 1.

At T=T$_{START}$ the processor 50 begins to acquire data from the A/D controller 58 (Block D). The data is recorded from the various channels with the current temperature in a matrix until T=T$_{END}$ (Block E). The detector output signals may be plotted as they are received. In this step the processor 50 monitors the measured temperature output from the temperature controller 54 and initiates the A/D readouts at the inputted temperature resolution. By example, if the inputted resolution is 1° C., then the A/D 58 is readout (and the optional MUX 56 cycled) at 1° C. temperature increments. Alternatively, the processor 50 can readout the A/D 58 at predetermined fixed temperature increments (e.g. 0.1° C.), and discard those readings that do not correspond to the inputted temperature resolution.

At Block F the processor 50 calculates the phase transition temperatures (e.g., melting point temperatures) using one or more of the techniques described above. At Block G the recorded data and melting points are outputted to the user, and the system cycles back to Block A to begin another series of measurements.

Having thus described the construction and operation of presently preferred embodiments of this invention, it will be understood by those having skill in the art that a number of modifications can be made to these presently preferred embodiments. By example only, other wavelengths, component types, numbers of capillary chambers, heater block geometries, and so forth can be employed, and such modifications will still fall within the scope of the teaching of this invention.

Thus, while the invention has been particularly shown and described with respect to preferred embodiments thereof, it will be understood by those skilled in the art that changes in form and details may be made therein without departing from the scope and spirit of the invention.

What is claimed is:

1. A structure for use in determining phase transition temperatures of a plurality of samples, comprising a metallic block having a plurality of holes, a first set of holes individual ones of which are made through a first surface of said block and have a diameter predetermined for accommodating a sample-containing tube therein, said block further having at least one second set of holes individual ones of which terminate at one of said holes of said first set, individual ones of said holes of said second set having a diameter predetermined for accommodating at least one optical fiber therein, and further comprising means for varying a temperature of said block.

2. A structure as set forth in claim 1, wherein said block has a generally circular cylindrical shape.

3. A structure as set forth in claim 1, wherein said block has a generally non-circular cylindrical shape.

4. A structure for use in determining phase transition temperatures of a plurality of samples, comprising a thermally conductive block having a plurality of openings made therein, including a first set of openings individual ones of which are made through a surface of said block for defining a plurality of sample-containing chambers within said block, a second set of openings individual ones of which terminate at one of said openings of said first set, individual ones of said second set of openings containing an optical fiber of a first set of optical fibers each having an output end for outputting light to one of said sample-containing chambers, a third set of openings individual ones of which terminate at one of said openings of said first set, individual ones of said third set of openings containing an optical fiber from a second set of optical fibers each having an input end for inputting light from one of said sample-containing chambers, and at least one fourth opening for containing an element that is thermally coupled to said block for varying a temperature of said block.

5. A structure as set forth in claim 4, wherein said block has a generally circular cylindrical shape.

6. A structure as set forth in claim 4, wherein said block has a generally bar-like shape.

7. A structure as set forth in claim 4, wherein an input end of individual ones of said optical fibers of said first set of optical fibers is optically coupled to one of a continuously or intermittently operated light emitting diode, solid state diode laser, or incandescent bulb.

8. A structure as set forth in claim 4, wherein an output end of individual ones of said optical fibers of said second set of optical fibers is optically coupled to a photodetector.

9. A structure as set forth in claim 4, wherein said output end of each of said plurality of optical fibers of said first set of optical fibers is located on a same side of said sample-containing chamber as said input end of one of said plurality of optical fibers of said second set of optical fibers.

10. A structure as set forth in claim 4, wherein said output end of each of said plurality of optical fibers of said first set of optical fibers is located on an opposite side of said sample-containing chamber as said input end of one of said plurality of optical fibers of said second set of optical fibers.

11. A structure as set forth in claim 4, wherein said block has a generally circular cylindrical shape, and wherein said sample-containing chambers are disposed in a circular fashion about a central axis of said block.

12. A structure as set forth in claim 4, wherein said block has a generally bar-like shape, and wherein said sample-containing chambers are disposed linearly along a longitudinal axis of said block.

13. A structure for use in determining phase transition temperatures of a plurality of samples, comprising a thermally conductive block having a plurality of openings made therein, including a first set of openings individual ones of which are made through a surface of said block for defining a plurality of sample-containing chambers within said block, a second set of openings individual ones of which terminate at one of said openings of said first set, individual ones of said second set of openings containing an optical fiber of a first set of optical fibers each having an output end for outputting light to one of said sample-containing chambers and an optical fiber from a second set of optical fibers each having an input end for inputting light from one of said sample-containing chambers, and at least one third opening for containing an element that is thermally coupled to said block for varying a temperature of said block.

14. A structure as set forth in claim 13, wherein said block has a generally circular cylindrical shape.

15. A structure as set forth in claim 13, wherein said block has a generally bar-like shape.

16. A structure as set forth in claim 13, wherein an input end of individual ones of said optical fibers of said first set of optical fibers is optically coupled to one of a continuously or intermittently operated light emitting diode, solid state diode laser, or incandescent bulb.

17. A structure as set forth in claim 13, wherein an output end of individual ones of said optical fibers of said second set of optical fibers is optically coupled to a photodetector.

18. A structure as set forth in claim 13, wherein said output end of each of said plurality of optical fibers of said first set of optical fibers is located on a same side of said sample-containing chamber as said input end of one of said plurality of optical fibers of said second set of optical fibers.

19. A structure as set forth in claim 13, wherein said block has one of a generally circular cylindrical shape, and wherein said sample-containing chambers are disposed in a circular fashion about a central axis of said block, or a generally bar-like shape, and wherein said sample-containing chambers are disposed linearly along a longitudinal axis of said block.

\* \* \* \* \*